US010980910B2

(12) United States Patent
Jurak et al.

(10) Patent No.: US 10,980,910 B2
(45) Date of Patent: Apr. 20, 2021

(54) APPARATUS AND METHODS FOR OZONE GENERATION AND DEGRADATION (71) Applicant: Gene Therapy Systems, Inc., San Diego, CA (US)

(72) Inventors: Steven J. Jurak, San Diego, CA (US); Anthony M. Sorge, Sr., Rancho Santa Fe, CA (US); Anthony M. Sorge, Jr., Rancho Santa Fe, CA (US); Alan Greener, San Diego, CA (US)

(73) Assignee: Gene Therapy Systems, Inc., San Diego, CA (US)

( * ) Notice: Subject to any disclaimer, the term of this patent is extended or adjusted under 35 U.S.C. 154(b) by 274 days.

(21) Appl. No.: 15/995,468

(22) Filed: Jun. 1, 2018

(65) Prior Publication Data
US 2019/0030204 A1 Jan. 31, 2019

Related U.S. Application Data (60) Continuation of application No. 15/488,755, filed on Apr. 17, 2017, now Pat. No. 9,987,388, which is a division of application No. 14/151,608, filed on Jan. 9, 2014, now Pat. No. 9,623,140.

(60) Provisional application No. 61/751,125, filed on Jan. 10, 2013.

(51) Int. Cl.
A61L 9/22 (2006.01)
A61L 2/20 (2006.01)

(52) U.S. Cl.
CPC ............... A61L 9/22 (2013.01); A61L 2/202 (2013.01)

(58) Field of Classification Search
CPC ..................... A61L 9/22; A61L 2/202
See application file for complete search history.

(56) References Cited

U.S. PATENT DOCUMENTS

| | | | |
|---|---|---|---|
| 2,453,435 A | 11/1948 | Haystad | |
| 5,024,766 A * | 6/1991 | Mahmud | C02F 1/008 210/142 |
| 5,368,816 A | 11/1994 | Detzer | |
| 6,481,219 B2 | 11/2002 | Palermo | |
| 6,485,978 B1 | 11/2002 | Kirckof et al. | |
| 7,407,624 B2 | 8/2008 | Cumberland | |
| 7,693,687 B2 | 4/2010 | Lev-Ami et al. | |
| 7,982,625 B2 | 7/2011 | Brochu et al. | |
| 8,236,236 B2 * | 8/2012 | Garner | A61L 2/10 422/186.07 |
| 8,354,057 B2 | 1/2013 | Heselton | |
| 8,865,065 B2 * | 10/2014 | Kain | A61L 2/24 422/28 |
| 9,623,140 B2 | 4/2017 | Jurak et al. | |
| 9,987,388 B2 | 6/2018 | Jurak et al. | |
| 2002/0058001 A1 | 5/2002 | Wu | |
| 2003/0127506 A1 | 7/2003 | Braun | |
| 2003/0152480 A1 | 8/2003 | Sham | |
| 2004/0047776 A1 | 3/2004 | Thomsen | |
| 2004/0202570 A1 | 10/2004 | Nadkarni | |
| 2004/0262241 A1 | 12/2004 | Socha | |
| 2005/0123436 A1 * | 6/2005 | Cumberland | A61L 9/22 422/5 |
| 2008/0031770 A1 | 2/2008 | Heselton | |
| 2008/0159910 A1 | 7/2008 | Dick et al. | |
| 2008/0213125 A1 | 9/2008 | Boast | |
| 2008/0213128 A1 * | 9/2008 | Rudy | A61L 2/10 422/24 |
| 2008/0310992 A1 | 12/2008 | Heselton | |
| 2010/0152911 A1 | 6/2010 | Brochu et al. | |
| 2010/0178196 A1 * | 7/2010 | Garner | A61L 2/24 422/4 |
| 2011/0008205 A1 * | 1/2011 | Mangiardi | A61L 9/015 422/23 |
| 2011/0268606 A1 | 11/2011 | Glazer et al. | |
| 2012/0020830 A1 | 1/2012 | Boast et al. | |
| 2012/0063949 A1 | 3/2012 | Jennings | |
| 2012/0316402 A1 | 12/2012 | Salapatek et al. | |

(Continued)

FOREIGN PATENT DOCUMENTS

CN 103977441 8/2014

OTHER PUBLICATIONS

Chemical Sampling Information | Ozone; NIOSH Pocket Guide to Chemical Hazards; United States Department of Labor Occupational Safety & Health Administration; OSHA IMIS Code No. 1980; Jan. 6, 2012; www.osha.gov/dts/chemicalsampling/data/CH_259300.html.

(Continued)

Primary Examiner — Regina M Yoo
(74) Attorney, Agent, or Firm — Knobbe, Martens, Olson & Bear, LLP (57) ABSTRACT Devices and methods for sterilizing an enclosed space using ozone are disclosed herein. Various embodiments of the devices and methods also provide for accelerated degradation of the ozone upon sterilization. In some embodiments, a disclosed sterilization unit includes a first housing defining an ozone generation cavity, an ozone generator disposed within the ozone generation cavity, a second housing defining an ozone degradation cavity, and an ozone degrader disposed within the ozone degradation cavity. The sterilization unit of various embodiments is configured to cycle air between the enclosed space and the ozone generation cavity during an ozone generation cycle to sterilize the enclosed space; similarly, the unit is further configured to cycle air between the enclosed space and the ozone degradation cavity during an ozone degradation cycle to return the air within the enclosed space to safe ozone levels.

18 Claims, 6 Drawing Sheets (56) References Cited

U.S. PATENT DOCUMENTS

| | | |
|---|---|---|
| 2013/0183749 A1 | 7/2013 | Aamodt et al. |
| 2013/0224072 A1 | 8/2013 | Glazer et al. |
| 2014/0193296 A1 | 1/2014 | Jurak et al. |
| 2014/0234165 A1 | 8/2014 | Glazer et al. |
| 2017/0072082 A1 | 3/2017 | Jurak et al. |
| 2017/0281823 A1 | 10/2017 | Jurak et al. |

OTHER PUBLICATIONS

English Translation of CN-103977441-A (Year: 2014).

* cited by examiner

APPARATUS AND METHODS FOR OZONE GENERATION AND DEGRADATION

CROSS-REFERENCE TO RELATED APPLICATION

The present application is a continuation of U.S. patent application Ser. No. 15/488,755, filed Apr. 17, 2017 and scheduled to issue as U.S. Pat. No. 9,987,388 on Jun. 5, 2018, which is a divisional of U.S. patent application Ser. No. 14/151,608, filed Jan. 9, 2014, and issued as U.S. Pat. No. 9,623,140 on Apr. 18, 2017, which claims priority under 35 U.S.C. § 119(e) to U.S. Provisional Patent Application No. 61/751,125, filed on Jan. 10, 2013. The disclosures of all of the above-referenced prior applications, publications, and patents are considered part of the disclosure of this application, and are incorporated by reference herein in their entirety.

BACKGROUND

Field

The present disclosure relates to decontamination systems and methods, and particularly, to systems and methods for sterilizing enclosed spaces through ozone generation.

Description of the Related Art

The removal of harmful or irritating contaminants, such as, for example, bacteria, viruses, bacteriophages, molds, spores, and cigarette smoke particulates, is a common goal in many areas where such contaminants proliferate. Within many environments, such as, for example, hospital rooms, airplanes, gyms, hotel rooms, rental cars, and laboratory and medical equipment, the presence of such contaminants can lead to harmful and/or disruptive results. For example, in hospital rooms and other healthcare facilities, sick patients introduce illness-causing bacteria and viruses into the air regularly. The presence of such contaminants is particularly dangerous in healthcare facilities where many patients have compromised immune systems that render them more susceptible to the contaminants' potentially adverse health effects. Additionally, in laboratory settings, spores, mold, bacteria, viruses, bacteriophages, and other foreign biological materials can contaminate test cultures, leading to inaccurate test results, costly delays, and potentially, loss of non-reproducible parent cultures.

Various methods currently exist for decontaminating enclosed spaces. In one method, a spray disinfectant is sprayed onto the surfaces of an enclosed space and wiped away. This method is time-intensive, requires frequent repetition, and limits disinfection to accessible surfaces. Biological materials present in the air and on difficult to reach surfaces often remain untouched. Additionally, commonly-used disinfecting agents are either limited in effectiveness or cytotoxic. Such a method may expose individuals doing the cleaning to chemicals harmful to their health. In another method, an ultraviolet radiator is used to disinfect a small enclosed space, such as a laboratory incubator or laboratory laminar flow hood. In such a method, disinfection is only possible in places directly exposed to the ultraviolet light. Steam-in-place sterilization is available in some laboratory settings, such as, for example, in laboratory hoods, incubators, and reaction vessels; however, the method is impractical in many environments. Steam-in-place sterilization can only be used within equipment capable of withstanding moisture and extremely high temperatures (approximately 100-180 degrees Celsius). Additionally, steam-in-place sterilization requires the installation of expensive steam-producing equipment. Other sterilization methods, such as sterilization within an ozone chamber or autoclave chamber are designed to sterilize objects placed within a sterilization chamber, making the method unusable for the decontamination of fixtures, rooms, large equipment, and other immobile and/or bulky items.

SUMMARY

A need exists for an effective, safe, convenient, and relatively low-cost sterilization method capable of thoroughly sterilizing an enclosed space. The present disclosure describes devices and methods for achieving at least some of these objectives. Methods and devices described herein are directed towards eliminating potentially harmful contaminants, such as, for example, bacteria, bacteriophages, molds, spores, viruses, and/or other particulates from an enclosed space. Such decontamination is achieved through the generation and release of ozone into the enclosed space. Various embodiments of the devices and methods described herein further provide for accelerated degradation of the ozone upon sterilization in order to quickly return the air in the enclosed space to safe ozone levels.

The embodiments disclosed herein each have several innovative aspects, no single one of which is solely responsible for the desirable attributes mentioned above. Without limiting the scope, as expressed by the claims that follow, the more prominent features will be briefly disclosed here. After considering this discussion, one will understand how the features of the various embodiments provide several advantages over current sterilization devices and methods.

One aspect of the disclosure is a sterilization unit for decontaminating an enclosed space. In some embodiments, the sterilization unit includes a first housing defining an ozone generation cavity, a second housing defining an ozone degradation cavity, an ozone generator disposed within the ozone generation cavity and configured to ozonize air that enters the ozone generation cavity, and an ozone degrader disposed within the ozone degradation cavity and configured to remove ozone from air within the ozone degradation cavity. In some such embodiments, the first housing and the second housing are integrated to form a single housing unit. In other embodiments, the first housing and the second housing are physically distinct and/or separated. For example, in one aspect, the first housing and the second housing are not integrated into a single housing unit and are located some distance away from each other. The first housing and the second housing can be located at different locations within the enclosed space to be decontaminated. In some aspects, the sterilization unit includes a first housing and a second housing that are physically located a distance away from each other within the enclosed space, such as but not limited to 1, 2, 3, 4, 6, 8, 10, 12, or more feet from each other. In some embodiments, the first housing and the second housing are physically located a distance away from each other within the enclosed space by a distance of between about 6 inches and about 12 inches. In one non-limiting example, in one embodiment of the sterilization unit, the first housing defining an ozone generation cavity is located near the top of an enclosed space to be decontaminated, while the second housing defining the ozone degradation cavity is located near the base of the enclosed space.

In some embodiments, the sterilization unit further includes a first air-moving component positioned in or next to the ozone generation cavity. The first air-moving component can be configured to move air from the enclosed space into a first inlet, through the ozone generation cavity, and out a first outlet. In some embodiments, the sterilization unit also includes a second air-moving component positioned in or next to the ozone degradation cavity. The second air-moving component can be configured to move air from the enclosed space into a second inlet, through the ozone degradation cavity, and out a second outlet.

In some embodiments, the sterilization unit further includes a processor that controls the ozone generator, the first air-moving component, and the second air-moving component in order to initiate and terminate an ozone generation cycle and an ozone degradation cycle. In some such embodiments, the sterilization unit also includes a user interface configured to receive inputs from a user and send command outputs to the processor. Additionally or alternatively, in some embodiments, the sterilization unit includes a battery to supply power to the sterilization unit.

Some embodiments of the sterilization unit also include a vortex plate positioned within the ozone degradation cavity. The vortex plate is configured to induce at least partially vortical flow of the air passing through the ozone degradation cavity.

A dust filter is disposed in the first inlet of the sterilization unit in some embodiments; in other embodiments, the dust filter is disposed in the ozone generation cavity between the first inlet and the ozone generator. Other embodiments may have no dust filter.

In some embodiments of the sterilization unit, the first and second air-moving components are selected from the group consisting of: a fan and an air blower. In other embodiments, different air-moving components known to one having skill in the art may be used.

The ozone generator of some embodiments is selected from the group consisting of: a corona discharge ozone generator, an ultraviolet ozone generator, and a vacuum-ultraviolet ozone generator. In other embodiments, a different ozone generating device known to one having skill in the art is used. In some embodiments, the ozone generator includes a plurality of ceramic plates with each of the ceramic plates at least partially coated or wrapped with a layer comprising a heavy metal. In some such embodiments, the layer at least partially coating or wrapping around a ceramic plate includes mesh formed of a metal selected from the group consisting of: steel, copper, nickel, cobalt, zinc, iron, silver, gold, and any combination thereof. The ozone generator of some embodiments is configured to produce a gas that includes both ozonized air and heavy metal ions. In some such embodiments, the ozone generator is configured to produce a gas that includes ozonized air and silver ions.

The ozone degrader of some embodiments is selected from the group consisting of: an ozone oxidation catalyst, a catalytic filter, a filter and any combination thereof. In other embodiments, a different ozone degrading device known to one having skill in the art is included in the sterilization unit. In some embodiments, the ozone degrader is formed, at least in part, of activated carbon. The ozone degrader of some embodiments includes a plurality of filters. In some such embodiments, the sterilization unit includes activated carbon-based materials compressed between the plurality of filters.

Another aspect of the disclosure is a method of decontaminating an enclosed space using any embodiment of the sterilization unit described above. In some embodiments, the method includes moving air containing oxygen from the enclosed space into the ozone generation cavity using a first air-moving component to bring at least some of the air into contact with the ozone generator, converting at least some of the oxygen in the ozone generation cavity into ozone, discharging ozonized air into the enclosed space at least until the enclosed space reaches a measurable ozone concentration, moving the ozonized air from the enclosed space into the ozone degradation cavity using a second air-moving component to bring at least some of the ozonized air into contact with the degrader, converting at least some of the ozonized air into deozonized air, and discharging deozonized air into the enclosed space at least until the enclosed space reaches a safe concentration of ozone.

A further aspect of the disclosure is another method of decontaminating an enclosed space. In some embodiments, the method first includes providing a sterilization unit. The sterilization unit of some such embodiments includes a housing, which defines an ozone generation cavity having a first inlet and first outlet, and an ozone degradation cavity having a second inlet and second outlet, an ozone generator disposed within the ozone generation cavity, a first air-moving component positioned in or next to the ozone generation cavity, an ozone degrader disposed within the ozone degradation cavity, and a second air-moving component positioned in or next to the ozone degradation cavity. Using the provided sterilization unit, the method of some embodiments further includes activating the first air-moving component to move air containing oxygen from the enclosed space into the ozone generation cavity, thereby bringing air into contact with the ozone generator, activating the ozone generator to convert at least some of the oxygen in the ozone generation cavity into ozone, discharging ozonized air into the enclosed space at least until the enclosed space reaches a measurable ozone concentration, activating the second air-moving component to move the ozonized air from the enclosed space into the ozone degradation cavity, thereby bringing the ozonized air into contact with the degrader to produce deozonized air, and discharging deozonized air into the enclosed space at least until the enclosed space reaches a safe concentration of ozone.

In some embodiments of the methods disclosed herein, the measurable ozone concentration is defined as an ozone concentration above 0.1 ppm. In some embodiments, the measurable ozone concentration is defined as an ozone concentration above 0.01 ppm. In some embodiments, the measurable ozone concentration is defined as an ozone concentration above 0.02 ppm. In some embodiments, the measurable ozone concentration is defined as an ozone concentration between about 0.01 to about 0.02 ppm. In some embodiments, the measurable ozone concentration is defined as an ozone concentration between about 0.01 to about 0.1 ppm. Further, in some embodiments disclosed herein, the safe ozone concentration is defined as an ozone concentration below 0.1 ppm. In some embodiments, the safe ozone concentration is defined as an ozone concentration up to 0.2 ppm for no more than 2 hours of exposure. In some embodiments, the safe ozone concentration is defined as an ozone concentration up to 0.1 ppm for 8 hours per day of exposure doing light work. In some embodiments, the safe ozone concentration is defined as an ozone concentration up to 0.08 ppm for 8 hours per day of exposure doing moderate work. In some embodiments, the safe ozone concentration is defined as an ozone concentration up to 0.05 ppm for 8 hours per day of exposure doing heavy work.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting. Throughout the drawings, similar symbols typically identify similar components, unless context dictates otherwise. The relative dimensions of the following figures may not be drawn to scale.

DETAILED DESCRIPTION OF CERTAIN EMBODIMENTS

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and form part of this disclosure.

The terminology used herein is for the purpose of describing particular embodiments only and is not intended to be limiting of the disclosure. It will be understood by those within the art that if a specific number of a claim element is intended, such intent will be explicitly recited in the claim, and in the absence of such recitation, no such intent is present. For example, as used herein, the singular forms "a", "an" and "the" are intended to include the plural forms as well, unless the context clearly indicates otherwise. As used herein, the term "and/or" includes any and all combinations of one or more of the associated listed items. It will be further understood that the terms "comprises," "comprising," "includes," "including," "haves," and "having," when used in this specification, specify the presence of stated features, integers, steps, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list.

To assist in the description of the devices and methods described herein, some relational terms are used. "Connected" and "coupled," and variations thereof, as used herein, include direct connections, such as being contiguously formed with or attached directly to, on, within, etc. another element, as well as indirect connections where one or more elements are disposed between the connected elements. "Connected" and "coupled" may refer to a permanent or non-permanent (i.e., removable) connection. "Secured" and variations thereof as used herein include methods by which an element is directly fastened to another element, such as being glued, screwed or otherwise affixed directly to, on, within, etc. another element, as well as indirect means of securing two elements together where one or more elements are disposed between the secured elements.

A need exists for an effective, safe, convenient, and relatively low-cost sterilization method capable of thoroughly sterilizing an enclosed space. The present disclosure describes devices and methods directed towards eliminating potentially harmful contaminants, such as, for example, bacteria, bacteriophages, molds, and viruses from an enclosed space using ozone. In some embodiments, the contaminants can be selected from one or more of the following: *G. stearothermophilus*, *B. atrophaeus*, *B. subtilis*, *B. anthrax* (and spores), *B. cereus*, *B. spizizenii*, *C. difficile*, *S. aureus*, *Propionibacterium acnes*, *S. pyogenes*, *Acinobacter baumannii*, *Enterococus faecalis*, *E. coli*, *Haemmophilus influenzae*, *Klebesiella pneumoniae*, *Legionella pneumophila*, *Pseudomonas aeruginosa*, *Mycobacterium*, *smegmatis*, *S. mutans*, *S. epidermidis*, *S. and C. pneumoniae*, *B. anthrasis*, *C. trachomatis*, Murine Novovirus, *Norovirus*, Feline calicivirus (FCV), Eurotium (Xerophile), *Cladosporium* spp., *Stachybotrys* spp., and *Aspergillus niger*.

Advantageously, ozone is a powerful oxidant known to have a broad spectrum of activity, capable of killing bacteria, bacteriophages, molds, viruses, and fungi and eliminating many odors and environmental particulates. Additionally, ozone is gaseous, and thus, able to flow through ventilation shafts and filters and difficult-to-reach places for thorough sterilization of enclosed spaces. Moreover, ozone is relatively easy to generate from a widely accessible compound—oxygen, and similarly, ozone degrades relatively easily back down to a stable and benign compound—oxygen.

In water, ozone has been shown to be a highly effective disinfectant with a relatively short half-life (of approximately 8-30 minutes); thus, it is commonly used to disinfect swimming pools and water supplies. Ozone is also an effective disinfectant in non-aqueous settings; however, ozone is less frequently used to disinfect the air, because the powerful oxidant has a half-life in the air as long as 36-72 hours. Ozone's oxidative nature makes it toxic to humans. The U.S. Occupational Safety and Health Administration (OSHA) limits acceptable ozone exposure in the workplace to under 0.1 ppm per workday.

Accordingly, various embodiments of the methods and devices disclosed herein provide for: (1) the sterilization of an enclosed space through ozone generation, and (2) accelerated degradation of the ozone upon sterilization. Various embodiments of the methods and devices are automated, allowing for the generation and degradation of ozone with minimal human involvement. Such devices and methods may limit workers' exposure to ozone while also reaching sterilization-achieving ozone levels.

Figure 1A:
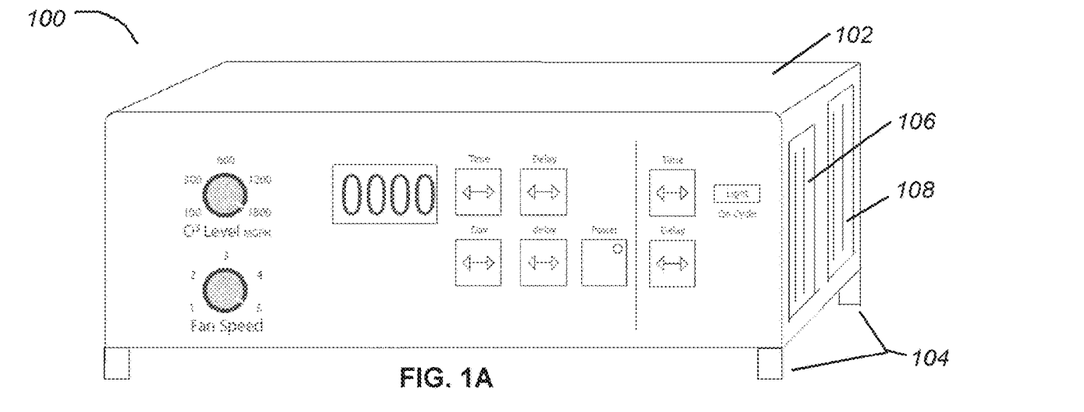
FIG. 1A provides a perspective view of one embodiment of a sterilization unit.

FIG. 1A provides a perspective view of one embodiment of a sterilization unit 100. The sterilization unit 100 can be an ozone generation and degradation unit. In the embodiment of FIG. 1A, the sterilization unit 100 is a semi-mobile unit having a single outer housing 102 and feet 104 and configured for placement on a shelf or floor of an enclosed space. In other embodiments, the sterilization unit 100 is a fully mobile unit having features to facilitate movement of the unit, such as, for example, one or more handles and/or one or more wheels. In other embodiments, the sterilization unit 100 is a semi-permanent or fully permanent fixture, which can be installed within an enclosed space. For example, in some embodiments, the sterilization unit 100 is placed onto a shelf within a piece of laboratory equipment, such as a laminar flow hood, a cell culture chamber, or a refrigerator. In other embodiments, the sterilization unit 100 is configured to be carried or rolled into hospital rooms, hotel rooms, gym locker rooms, and other enclosed spaces. In still other embodiments, the sterilization unit 100 is configured to be installed in an enclosed space such that it is affixed to or within a wall, ceiling, or floor of a room or piece of laboratory equipment.

The sterilization unit 100 of various embodiments is configured to decontaminate and/or sterilize an enclosed space by generating the powerful oxidant, ozone, and releasing the ozone into the enclosed space. In some embodiments, the enclosed space is air-tight, such as, for example, in a cell culture chamber or a laminar flow hood. In other embodiments, the enclosed space is not air-tight. In some such embodiments, the enclosed space is a room or portion of a dwelling having walls, doorways, and/or windows that do not fully seal in gases, such as, for example, in hotel rooms, hospital rooms, medical facilities, gyms, and bathrooms. In some embodiments, the enclosed space may be substantially but not fully enclosed, such as, for example, the space within a gym locker, wherein the locker has holes on its front face. In other embodiments, the enclosed space is an automobile. One having skill in the art will appreciate that the invention is not limited by the location in which it is used, and it is herein contemplated that the sterilization unit 100 may be used in any partially, substantially, and/or fully enclosed space that is in need of sterilization and capable of safely handling brief periods of ozone exposure. As non-limiting examples, the sterilization unit of various embodiments may be used to: disinfect the inner chambers of laboratory and medical equipment, eliminate smoke particulates and odors from rental cars and hotel rooms, and kill germs present in hospital rooms, medical facilities, and gyms.

In various embodiments, the sterilization unit 100 generates ozone during an ozone generation cycle. In such a cycle, air is guided from the enclosed space through one or more air vents (not visible) on a first side of the sterilization unit 100 and into an ozone generation cavity (not visible in FIG. 1A) where oxygen in the air is converted to ozone. The ozonized air is then dispelled out one or more air vents 106 on a second side of the sterilization unit 100 back into the enclosed space. The oxidative and reactive ozone in the air has a sterilizing effect within the enclosed space. An ozone generation cycle may continue for a specific amount of time or until a specific ozone concentration is reached within the enclosed space.

In order to limit potential exposure to ozone, the sterilization unit 100 of various embodiments is also configured to accelerate ozone degradation in the enclosed space. During ozone degradation, the oxidative and reactive ozone is broken down to the stable and safe compound, oxygen. In various embodiments, the sterilization unit 100 accelerates ozone degradation at least during an ozone degradation cycle once sterilization is complete. In such a cycle, ozonized air is guided from the enclosed space through one or more air vents (not visible) on a first side of the sterilization unit 100 and into an ozone degradation cavity (not visible in FIG. 1A) where the ozone in the air is converted back to a stable oxygen molecule. The de-ozonized air is then dispelled out one or more air vents 108 on a second side of the sterilization unit 100 back into the enclosed space. Through this cycle, ozone is removed from the air, thereby making the air safe for human exposure.

Figure 1B:
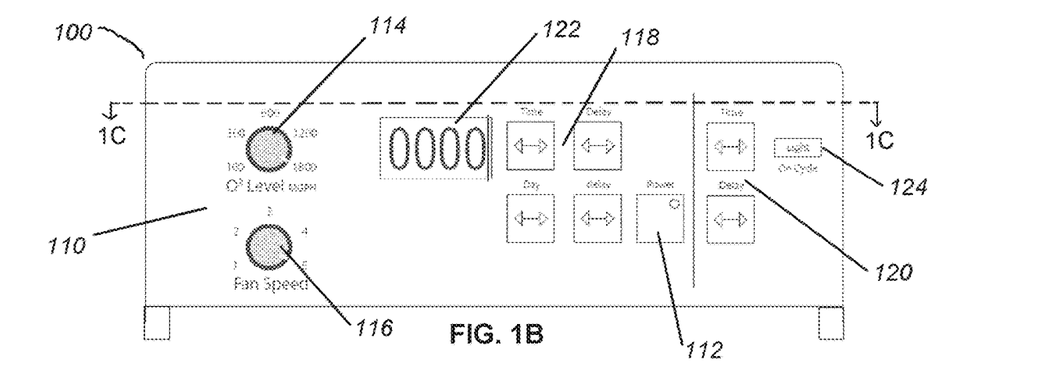
FIG. 1B provides a front view of the sterilization unit of FIG. 1A.

Numerous attributes of these ozone generation and degradation cycles can be controlled by a user through a user interface, such as through the control panel 110 shown in FIG. 1B. In various embodiments, a user can control one or more of the following settings through the user interface 110 of the sterilization unit 100: fan speed, ozone generation intensity, length of ozone generation and/or ozone degradation cycles, and start time of ozone generation and/or ozone degradation cycles. For example, with the control panel 110 of FIG. 1B, a user can power the unit 100 on and off by pressing a power button 112. In the depicted embodiment, a user can turn an ozone level knob 114 to control the intensity of the ozone generator and regulate the rate of ozone production, as measured, for example, in milligrams per hour. A user can also turn a fan speed knob 116 to regulate the speed at which air is pulled from an enclosed space into an ozone generation cavity. A series of buttons 118 also exist for setting the day and time at which an ozone generation cycle is to start. Alternatively, a user can press buttons 118 to program a delayed start. As a non-limiting example, in some environments, a user may turn on the sterilization unit 100 near the end of a work day by pressing the power button 112 and set a 30-minute delay so that ozone production does not begin for 30 minutes, giving all personnel time to leave the enclosed space. The buttons 118 can also be manipulated to set the duration of the ozone generation cycle. In the present embodiment, a series of buttons 120 also exist for controlling the ozone degradation cycle. A user can manipulate the buttons 120, for example, to set the duration of the ozone degradation cycle. Doing so sets the duration during which air-moving components present in the sterilization unit 100 actively move air through an ozone degradation cavity. A user may also toggle the buttons 120 to set a delayed start. For example, a user can program the sterilization unit 100 to begin blowing air through the ozone degradation cavity one hour (or any other desired length of time) after the ozone generation cycle has begun. Various displays may be present to alert users of the current status of the sterilization unit 100. For example, in FIG. 1B, the power button 112 contains a light, which is illuminated when the sterilization unit 100 is in an "on" state. A display 122 is also present to provide a countdown of the time remaining in an ozone generation cycle. In some embodiments the display 122 or other display (not shown) provides a countdown of the time remaining until an ozone generation cycle is scheduled to begin. An alert light 124 also illuminates when an ozone degradation cycle is in progress.

In various other embodiments, the user interface includes a touchscreen, physical buttons, keys, knobs, and/or any other input elements that are suitable for manipulating the settings of the sterilization unit and are known to one skilled in the art. In addition to receiving inputs from a user, the user interface is also designed to display outputs. The user interface of various embodiments includes one or more lights, visible messages and/or audible alarms to provide users with information about the status of the sterilization unit.

In another embodiment (not shown), a user can use various features of the user interface to input the cubic size of the enclosed space and a peak ozone concentration the user wishes to achieve within the enclosed space. In such an embodiment, the sterilization unit is programmed to calculate the appropriate run time for ozone generation, and optionally, for ozone degradation. In another embodiment (not shown), the sterilization unit is equipped with one or more sensors configured to detect the humidity, pressure, temperature, and/or current ozone level in the enclosed space. Such a sterilization unit is configured to calculate and set the appropriate run time for ozone generation and/or ozone degradation, based in part, on these parameters.

The user interface 110 of FIG. 1B is designed as an integrated control panel disposed on a front face of the sterilization unit 100. In other embodiments, the user interface is positioned on a top face or side face. In still other embodiments, the user interface is positioned on a separately located control panel, a remote control, or other device in wired or wireless communication with the sterilization unit. For example, in some embodiments, the sterilization unit is controllable through a user's cell phone or computer. In such embodiments, commands are sent to the sterilization unit from a remote user interface via radiofrequency, WiFi, Bluetooth, and/or near-field communications. The remote user interface may be positioned outside of the enclosed space while the remainder of the sterilization unit is disposed within the space.

In some embodiments of a sterilization unit, ozone generation and ozone degradation occur within separate cavities within an integrated unit. For example, as shown in the cross-sectional view of the sterilization unit 100 in FIG. 1C, ozone generation occurs within an ozone generation cavity 130 and ozone degradation occurs within an ozone degradation cavity 140. While air flow through the ozone generation cavity 130 and ozone degradation cavity 140 is separated, the two cavities are positioned next to each other and contained within the same outer housing 102. Thus, in some aspects, sterilization units described herein include an outer housing enclosing a first housing and a second housing, the first housing including an ozone generation cavity and the second housing including an ozone degradation cavity.

In other embodiments (not shown), the ozone generation cavity and the ozone degradation cavity are contained in separate, unattached housings. In such embodiments, the ozone generation cavity and the ozone degradation cavity can each be installed or positioned in different locations within the enclosed space. For example, in one aspect, the ozone generation cavity and the ozone degradation cavity are not integrated into an outer housing and are located some distance away from each other at different locations within the enclosed space to be decontaminated. Thus, embodiments of the sterilization unit described herein can include an ozone generation cavity and an ozone degradation cavity that are physically positioned a distance away from each other within the enclosed space, such as but not limited to 1, 2, 3, 4, 6, 8, 10, 12, or more feet away from each other. As a non-limiting example, in one embodiment of the sterilization unit, the ozone generation cavity is installed near the top of an enclosed space while the ozone degradation cavity is installed near the base or bottom of the enclosed space. In another non-limiting example, a first housing including an ozone generation cavity and a second housing including an ozone degradation cavity are not enclosed within the same outer housing. The first housing and the second housing in this example are located a distance away from each other at different locations within the enclosed space.

Figure 1C:
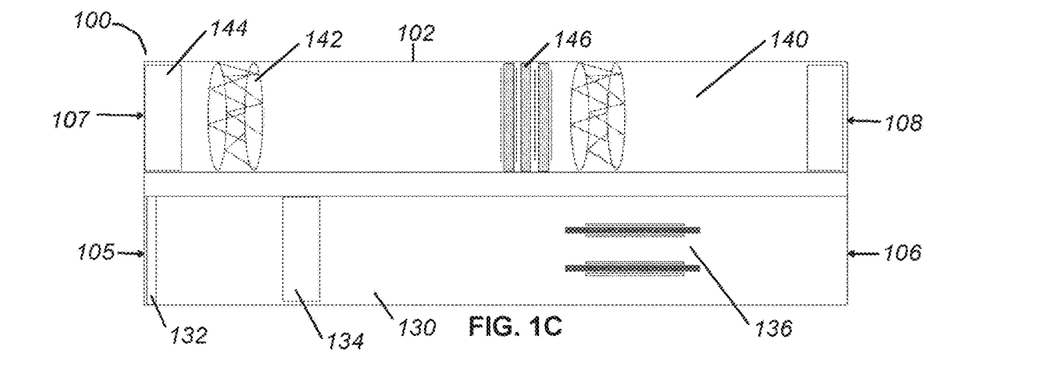
FIG. 1C provides a cross-sectional view of the sterilization unit of FIGS. 1A and 1B, as viewed along the cut-line provided in FIG. 1B.

Continuing with FIG. 1C, the ozone generation cavity 130 is positioned between a first inlet 105 and a first outlet 106. The first inlet 105 and outlet 106 each comprise one or more holes, slots, or other openings in the housing 102, through which air from the enclosed space can enter and exit, respectively, the ozone generation cavity 130. The ozone generation cavity 130 includes, at least, an ozone generator 136 disposed within the ozone generation cavity 130. In the depicted embodiment, an air filter 132 is positioned in the ozone generation cavity 130 between the first inlet 105 and the ozone generator 136. In other embodiments, the air filter 132 is positioned within or on the exterior side of the first inlet 105. The air filter 132 is configured to remove dust, dirt, and other large particulates from the air before the air reaches the ozone generator 136.

The ozone generation cavity 130 of FIG. 1C also includes a first air-moving component 134 disposed within the cavity 130. In some embodiments, a plurality of first air-moving components 134 are present within the cavity 130 and positioned between the first inlet 105 and the ozone generator 136. In other embodiments, a plurality of first air-moving components 134 are positioned in the cavity 130 between the ozone generator 136 and the first outlet 106. Other embodiments have one or more first air-moving components 134 on the inlet side of the ozone generator 136 and one or more first air-moving components 134 on the outlet side of the ozone generator 136. In still other embodiments, the one or more first air-moving components 134 may be positioned within or on the exterior side of the first inlet 105 and/or within or on the exterior side of the first outlet 106. In FIG. 1C, the first air-moving component is a fan. In other embodiments, the first air-moving component is an air blower or any other air-moving element know to one having skill in the art. When the first air-moving component 134 is in operation, it pushes or pulls air from the surrounding enclosed space through the first inlet 105 and the air filter 132, past the ozone generator 136, and out the first outlet 106. That is, in operation, the first air-moving component 134 cycles air between the enclosed space and the ozone generation cavity, helping to dispel ozone into the enclosed space.

As also shown in FIG. 1C, the ozone degradation cavity 140 is positioned between a second inlet 107 and a second outlet 108. The second inlet 107 and a second outlet 108 each comprise one or more holes, slots, or other openings in the housing 102, through which air from the enclosed space can enter and exit, respectively, the ozone degradation cavity 140. The ozone degradation cavity 140 of various embodiments includes, at least, an ozone degrader 146.

The ozone degradation cavity 140 of FIG. 1C also includes two vortex plates 142 and two second air-moving components 144. One having skill in the art will appreciate that in other embodiments, a different number of vortex plates 142 and/or second air-moving components 144 may be present, for example, zero, one, three, or four. Each of the vortex plates 142 and second air-moving components 144 may be positioned: within the ozone degradation cavity 140 between the second inlet 107 and the ozone degrader 146, within the ozone degradation cavity 140 between the ozone degrader 146 and the second outlet 108, in the second inlet 107, in the second outlet 108, or on the exterior side of the second inlet 107 or second outlet 108. In FIG. 1C, the second air-moving components 144 are fans. In other embodiments, air blowers or other air-moving elements are used. In various embodiments, the second air-moving components 144 are configured to push or pull air from the surrounding enclosed space through the second inlet 107, past the ozone degrader 146, and out the second outlet 108, thereby cycling air between the enclosed space and the ozone degradation cavity. The vortex plates 142, when present, are configured to generate at least partially vortical or turbulent airflow. By generating non-laminar airflow, more ozone within the air makes contact with the ozone degrader 146; such an arrangement may accelerate the rate of ozone degradation. In some embodiments, the vortex plates 142 are formed of a plurality of fixed fan fins. In other embodiments, other vortex-inducing designs are used.

In some embodiments, the sterilization unit 100 includes one or more shutters or valves (not shown) positioned within the second inlet 107, in the ozone degradation cavity 140, and/or on the exterior side of the second inlet 107 and/or second outlet 108. The one or more shutters or valves are configured to prevent air from flowing through the ozone degradation cavity 140 when an ozone degradation cycle is not in progress. For example, the one or more shutters or valves remain closed during ozone generation cycles, allowing large concentrations of ozone to build up within the enclosed space. After the ozone generation cycle terminates, the one or more shutters or valves open to initiate the ozone degradation cycle and allow air to cycle past the ozone degrader 146.

In addition to the components described above, various embodiments of the sterilization unit include a rechargeable battery, disposable batteries, and/or cords and a plug for receiving power from an external source. While such batteries, power cords, wiring, and internal electrical connections are not shown in FIG. 1C, it is to be understood and herein contemplated that these can be included and positioned in any suitable manner known to a person skilled in the art.

Figure 2A:
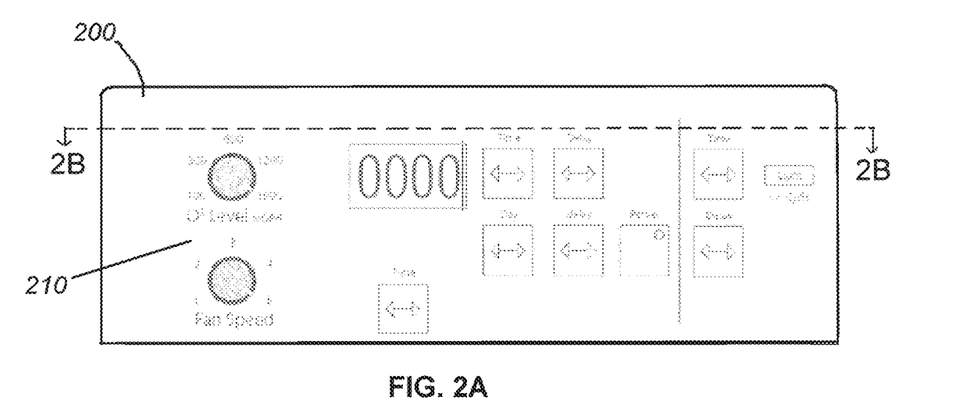
FIG. 2A provides a front view of another embodiment of a sterilization unit.

An additional embodiment of a sterilization unit 200 is provided in FIG. 2A. The sterilization unit 200 can be an ozone generation and degradation unit. In the provided embodiment, a user is able to adjust the buttons and knobs of the control panel 210 in order to set the ozone generation level and the fan speed, and the user may choose to set the values to correspond to particular dimensions and sterilization needs of the enclosed space. The user may also set the duration of the ozone generation cycle, the duration of the ozone degradation cycle, and/or a time delay for the start of the ozone generation and/or degradation cycles. Using such time delay features, a user may, for example, program the unit to begin the ozone generation cycle at the end of the day when no one is using or within the enclosed space. Upon reaching the set ozone level, the unit of various embodiments is programmed to end the ozone generation cycle and begin the ozone degradation cycle, and it may be programmed to terminate the ozone degradation cycle and return the enclosed space to safe ozone levels before anyone returns to the enclosed space the next day.

Figure 2B:
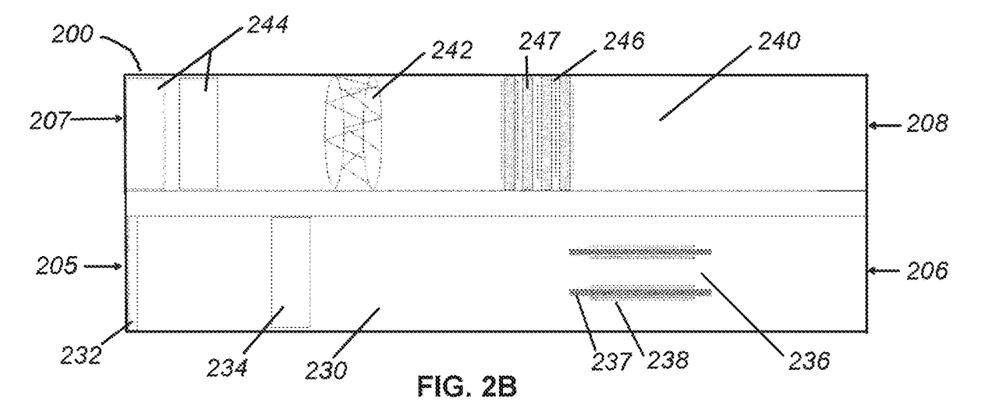
FIG. 2B provides a cross-sectional view of the sterilization unit of FIG. 2A.

As shown in the cross-sectional view of FIG. 2B, the ozone generation cavity 230 of FIG. 2B is positioned between a first inlet 205 and a first outlet 206 and includes an air filter 232, a first air-moving component 234, and an ozone generator 236. In one non-limiting example, the first air-moving component 234 includes a fan. Any ozone generator known to those skilled in the art may be used. In some embodiments, the ozone generator is a corona discharge ozone generator. In other embodiments, an ultraviolet ozone generator or a vacuum-ultraviolet ozone generator is used. In the embodiment depicted in FIG. 2B, the ozone generator 236 includes two ceramic plates 237, with each of the ceramic plates 237 at least partially coated or wrapped with a layer 238 comprising a heavy metal. Particularly, in FIG. 2B, each ceramic plate is partially surrounded by a stainless steel mesh 238 that is coated with a layer of pure silver. In other embodiments, the mesh 238 surrounding each ceramic plate 237 additionally or alternatively includes copper, nickel, cobalt, zinc, iron, gold, or any combination thereof. In such an arrangement, one of the ceramic plates 237 wrapped in a metallic mesh 238 forms an anode and the other ceramic plate 237 forms a cathode. In operation, a high voltage is applied across the anode and cathode arrangement, creating an electric field between the plates 237. As air passes through the electric field between the plates 237, the oxygen molecules present in the air become excited and some dissociate, forming unstable oxygen atoms. The oxygen atoms then react with other oxygen molecules to form ozone.

In some embodiments, the application of a voltage across the ceramic plates 237 also excites the heavy metal or metals that are at least surrounding or coating the plates 237. Such excitation may cause heavy metal ions to be produced and released into the enclosed space with the ozonized air. In the arrangement shown in FIG. 2B, the application of a high voltage to the ceramic plates 237 produces both ozone and silver ions. Silver ions have preliminarily been shown to have an antimicrobial effect, helping to augment the sterilizing effect of the ozone. With such an arrangement, even hard to kill biologic materials, such as T1 bacteriophages have been killed in experiments, as described in more detail below. The ozone generator of some embodiments is configured to produce a gas that includes both ozonized air and heavy metal ions. In some such embodiments, the ozone generator is configured to produce a gas that includes ozonized air and silver ions.

Continuing with FIG. 2B, the ozone degradation cavity 240 is positioned between a second inlet 207 and a second outlet 208, and includes one or more second air-moving components 244, a vortex plate 242, and an ozone degrader 246. In one non-limiting example, the one or more second air-moving components 244 include one or more fans. In one embodiment, the one or more second air-moving components 244 include two fans. Any ozone degrader capable of accelerating the breakdown of ozone to oxygen, which is known to those skilled in the art may be used. The ozone degrader 246 of some embodiments is selected from the group consisting of: an ozone oxidation catalyst, a catalytic filter, a filter and any combination thereof. For example, in some embodiments, the ozone degrader 246 is formed of a metal alloy catalyst, such as, for example, a manganese oxide, platinum-iridium, or platinum-palladium catalyst. In some embodiments, the ozone degrader is formed, at least in part, of activated carbon. In FIG. 2B, the ozone degrader 246 is formed of activated carbon-based filters 247 sandwiched closely together. The filters 247 are formed of mesh copper with activated carbon bound to the copper. In some embodiments, the activated carbon may be bound to a different metallic mesh. In other embodiments, a layer of activated carbon particles may be compressed between layers of metallic or non-metallic mesh or nonwoven fabric material. In FIG. 2B, four activated carbon-based filters are present. In other embodiments, one, two, three, or more activated carbon-based filters are used to convert ozone to oxygen.

Figure 3:
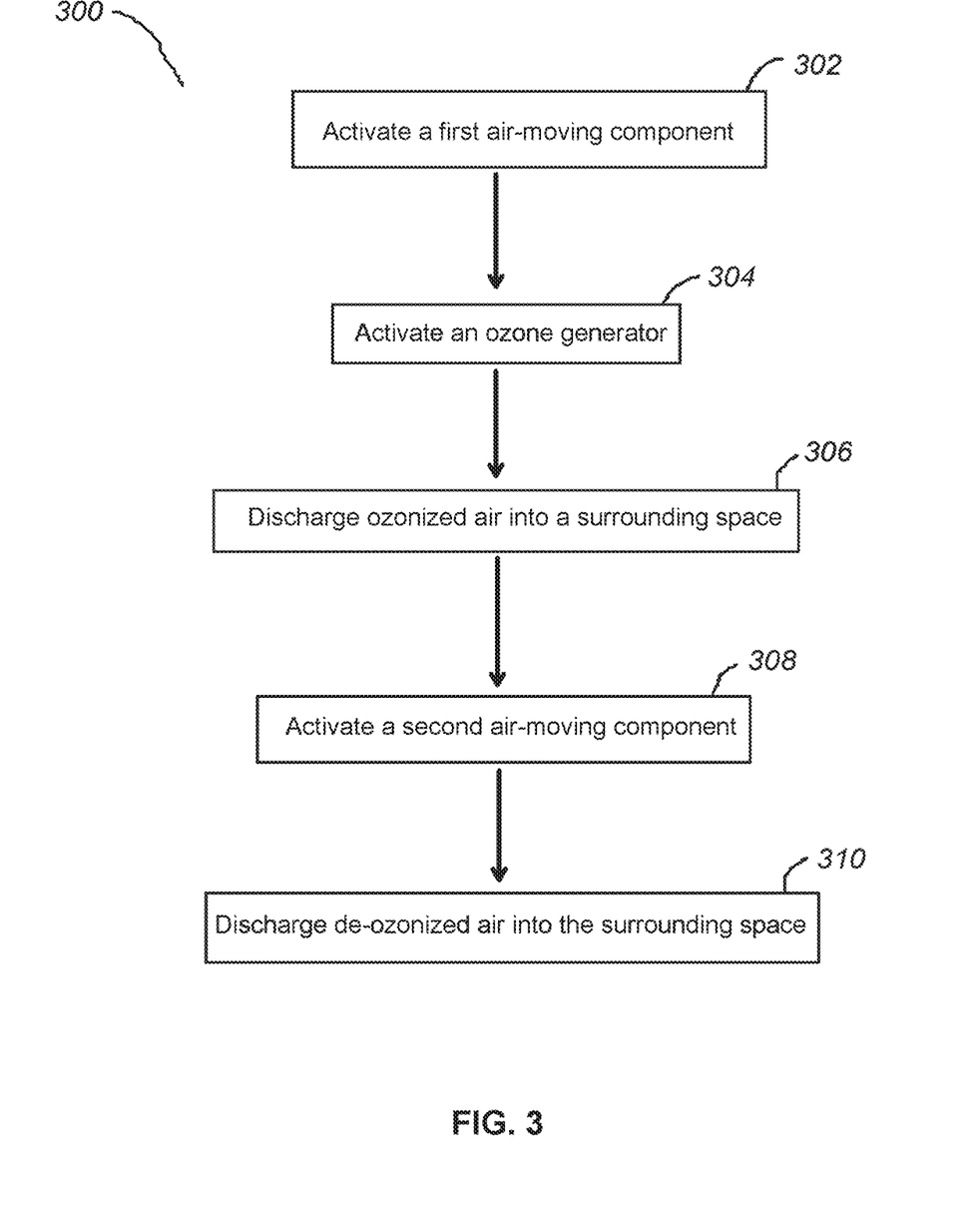
FIG. 3 provides a flow chart of one embodiment of a method of decontaminating and/or sterilizing an enclosed space.

FIG. 3 provides a flow chart 300 depicting one embodiment of a method of sterilizing and/or decontaminating an enclosed space using a sterilization unit, such as, for example, sterilization unit 100 or 200 positioned within the enclosed space. When describing the components used to perform the method, reference will be made to FIGS. 2A and 2B. Throughout the described embodiment, information and signals may be represented by voltages, currents, electromagnetic waves, magnetic fields or particles, optical fields or particles, or any combination thereof.

As shown at block 302, the sterilization unit 200 supplies electrical signals to a first air-moving component 234 positioned in or near the ozone generation cavity 230 in order to activate the first air-moving component 234. Activating the first air-moving component 234 moves air containing oxygen from the enclosed space into the ozone generation cavity 230 and into contact with an ozone generator 236. At block 304, the sterilization unit 200 supplies electrical signals to the ozone generator 236, which activates the ozone generator 236 and causes at least some of the oxygen in the air to convert to ozone. At block 306, ozonized air is discharged from the ozone generation cavity 230 into the enclosed space. The ozonized air exits the ozone generation cavity 230 through a first outlet 206. This discharge of ozonized air occurs in response to the continued operation of the first air-moving component 234. In some embodiments, this cycle of generating ozonized air and discharging it into the enclosed space is repeated until the air in the enclosed space reaches a measurable ozone concentration, such as, for example, 0.1 ppm. In other embodiments, the cycle continues for a set period of time or until the air in the enclosed space reaches an ozone concentration sufficient for sterilization, such as, for example, at least 60 ppm. In some embodiments, the cycle continues until the air in the enclosed space reaches an ozone concentration of at least 140 ppm. In some embodiments, the cycle continues until the air in the enclosed space reaches an ozone concentration of between about 140 and about 150 ppm. In some embodiments, the cycle continues until the air in the enclosed space reaches an ozone concentration of at least 325 ppm.

At block 308, the sterilization unit 200 supplies electrical signals to a second air-moving component 244 positioned in or near the ozone degradation cavity, thereby activating the second air-moving component 244. Activating the second air-moving component 244 moves ozonized air from the enclosed space into the ozone degradation cavity 240 and into contact with the ozone degrader 246. In various embodiments, the ozone degrader 246 is a filter or other non-electrical component, thus, the ozone degrader 246 does not require activation. Making contact with the ozone degrader 246 is sufficient to cause at least some of the ozone to convert to oxygen molecules, thereby reducing the ozone content in the air. At block 310, de-ozonized air is discharged into the enclosed space. The de-ozonized air exits the ozone degradation cavity 240 through a second outlet 208. This discharge of de-ozonized air occurs in response to the continued operation of the second air-moving component 244. In some embodiments, this cycle of discharging de-ozonized air into the enclosed space is repeated until the air in the enclosed space reaches a safe ozone concentration, such as, for example, a concentration of less than 0.1 ppm. In other embodiments, the cycle continues for a set period of time.

In some embodiments, information about when to initiate each of the blocks described above may be received from a user supplying inputs through a user interface 210. The steps of a method and functions described above, in connection with the embodiments disclosed herein, may be embodied directly in hardware, in a software module executed by a processor, or in a combination of the two. If implemented in hardware, the methods may be implemented or performed with, or controlled by, any suitable means capable of performing the operations, including a general purpose processor, a Digital Signal Processor (DSP), an Application Specific Integrated Circuit (ASIC), a Field Programmable Gate Array (FPGA), or other programmable logic device, discrete gate or transistor logic, discrete hardware components, or any combination thereof designed to perform the functions described herein. A general purpose processor may be a microprocessor, but in the alternative, the processor may be any processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

If any of the steps of a method or functions described above are implemented in software, the functions may be stored on or transmitted over as one or more instructions or code on a tangible, non-transitory computer-readable medium. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art. In some embodiments, a storage medium is coupled to the processor such that the processor can read information from, and write information to, the storage medium. In the alternative, the storage medium may be integral to the processor. Disk and disc, as used herein, includes compact disc (CD), laser disc, optical disc, digital versatile disc (DVD), floppy disk and blu ray disc where disks usually reproduce data magnetically, while discs reproduce data optically with lasers. Combinations of the above should also be included within the scope of computer readable media. The processor and the storage medium may reside in an ASIC. The ASIC may reside in a user terminal. In the alternative, the processor and the storage medium may reside as discrete components in a user terminal.

A similar method is performed by the embodiment of the sterilization unit 400 of FIGS. 4A-4D. The sterilization unit 400 can be an ozone generation and degradation unit. In the present embodiment, the user interface/control panel is separated from, and in wireless communication with, the remainder of the unit.

In the embodiment of FIGS. 4A-4D, the first inlet 405 into the ozone generation cavity 430 is positioned on the top face of the unit 400. The first outlet 406 to the ozone generation cavity 430 is positioned on the bottom face of the unit 400. Conversely, the second inlet 407 into the ozone degradation cavity 440 is positioned on the bottom face of the unit 400 and the second outlet 408 to the ozone degradation cavity 440 is positioned on the top face of the sterilization unit 400. In the depicted embodiment, the unit 400 is provided with feet 404 to elevate the sterilization unit 400 and provide for airflow between the bottom face of the unit and the enclosed space.

Advantageously, such a configuration may provide for more efficient ozone generation and degradation. Ozone is heavier than oxygen and has been found to largely settle to the bottom of an enclosed space. Accordingly, during the ozone generation cycle, oxygen-rich air, which largely rests above the ozone-rich air, can readily be pulled from above through the first inlet 405 on the top face of the sterilization unit 400. The ozonized air can then be dispelled downward through the first outlet 406 on the bottom face of the sterilization unit. The ozonized air can then settle near the bottom of the enclosed space. In this manner, oxygen-rich air, still in need of being ozonized, may be pulled into the ozone generation cavity 430 at a greater rate than the air that has already been ozonized, thus increasing the efficiency of the ozonizing process. Similarly, during the ozone degradation cycle, ozonized air, present in greater concentrations near the bottom of the enclosed space than the top of the enclosed space, can be pulled into the ozone degradation cavity 440 with greater efficiency by pulling the ozonized air through a second inlet 407 positioned on the bottom face of the sterilization unit 400 and expelling the de-ozonized air upward through a second outlet 408 positioned on the top face of the sterilization unit 400.

Figure 4A:
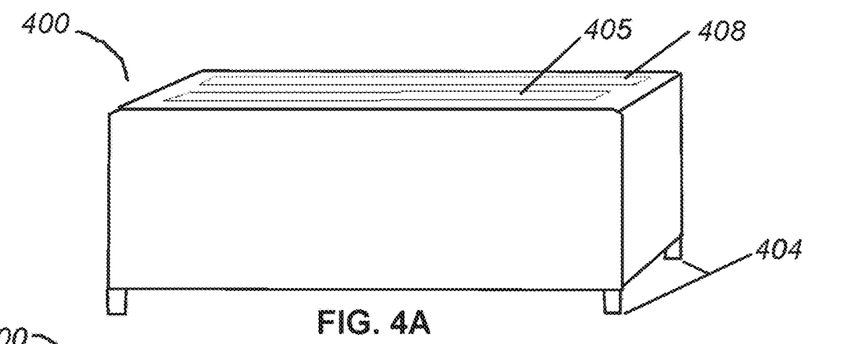
FIG. 4A provides a perspective view of an embodiment of a sterilization unit.
Figure 4B:
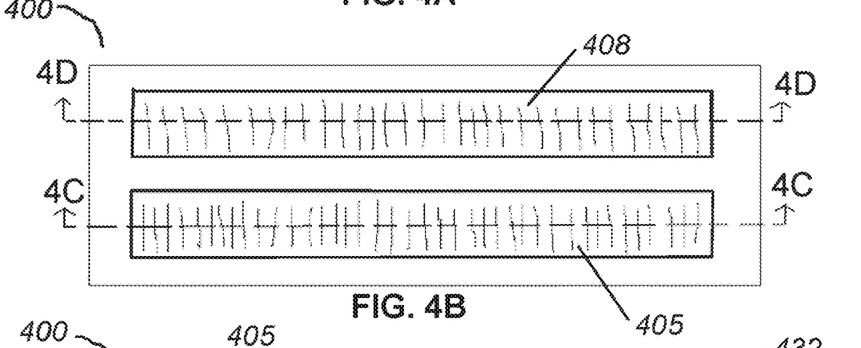
FIG. 4B provides a top view of the sterilization unit of FIG. 4A.
Figure 4C:
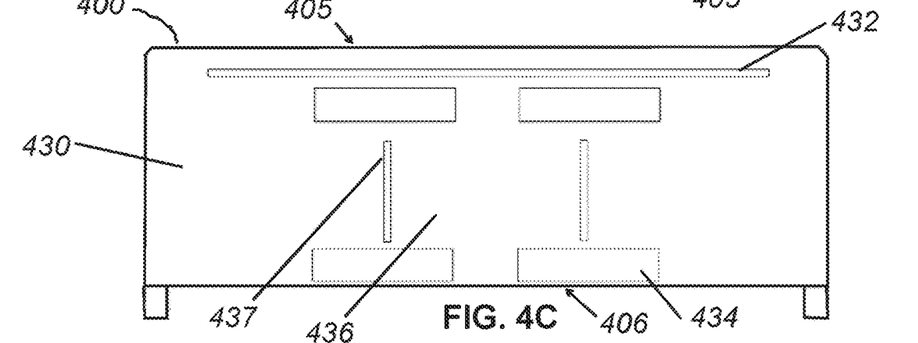
FIG. 4C provides a cross-sectional view of the sterilization unit of FIGS. 4A and 4B, as viewed along the corresponding cut-line of FIG. 4B.

As shown in the cross-section of the ozone generation cavity 430 in FIG. 4C, during the ozone generation cycle, a plurality of fans 434 operate to pull air through the first inlet 405, through an air filter 432, between the plates 437 of the ozone generator 436, and out the first outlet 406. During this time, the ozone generator 436 is also activated and a high voltage is present between the plates 437 of the ozone generator 436, so that at least some of the oxygen in the air passing between the plates 437 is converted to ozone. This cycle of ozone generation can be programmed to continue for a specified time or until a specified concentration of ozone is generated.

Figure 4D:
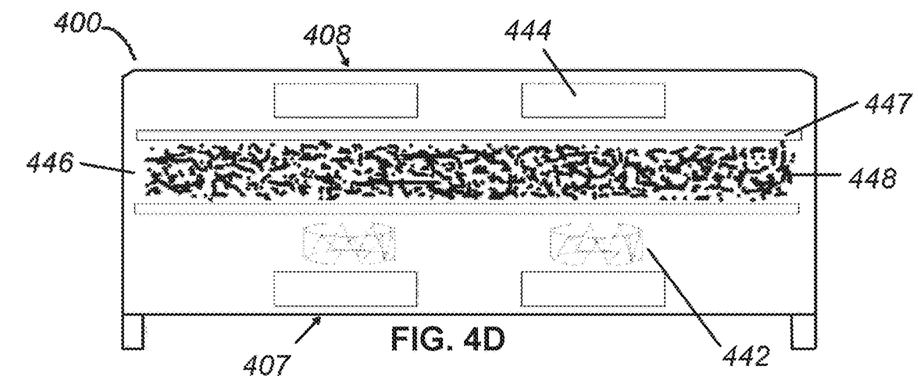
FIG. 4D provides an additional cross-sectional view of the sterilization unit of FIGS. 4A and 4B, as viewed along the corresponding cut-line of FIG. 4B.

As shown in the cross-section of the ozone degradation cavity in FIG. 4D, during the ozone degradation cycle, a plurality of fans 444 operate to pull air through: the second inlet 407, one or more vortex plates 442, and the ozone degrader 446, before being expelled out the second outlet 408. At least some of the ozonized air is de-ozonized as it passes through the ozone degrader 446. In FIG. 4D, the ozone degrader 446 includes a layer of activated carbon particles 448 compressed between two layers of copper mesh 447. In some embodiments, the particles are shaped like pellets. In other embodiments, the particles are shaped like granules, discs, chunks, or any other suitable shape known to those skilled in the art.

One embodiment of the sterilization unit was used in a series of experiments to test the efficacy of the unit. The experimental methods and results are described briefly below.

Experiment 1

In Experiment 1, an 1800 mg/hour ozone generator was placed in a 5.5 cubic feet cell culture. The ozone level within the chamber was monitored using a calibrated ozone analyzer. Ozone measurements were captured every 10 seconds. The experimental results, as represented by ozone level over time, are provided in the line graph 500 of FIG. 5A. In test #1, represented by line 510, the ozone generator was run for 80 minutes and achieved a peak ozone concentration within the cell culture chamber of approximately 325 ppm. After the ozone generator was turned off, the ozone was left to break down naturally within the enclosed cell culture chamber. It took approximately 28 hours for the ozone to breakdown to 0.01 ppm ozone.

Figure 5A:
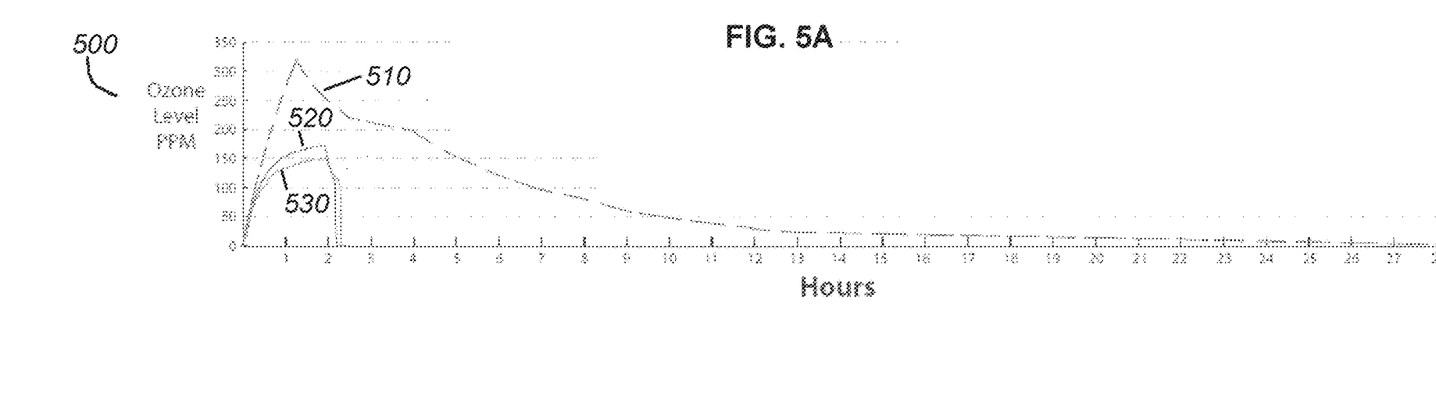
FIG. 5A provides a line graph of ozone level per hour, demonstrating the efficacy of the ozone generation and degradation unit of one embodiment.

In tests #2 and #3, represented by lines 520 and 530, respectively, both the ozone generator and an ozone degrader were present in the cell culture chamber. The ozone degrader was formed of three activated carbon filters. With the ozone degrader present, the ozone generator was unable to achieve the peak ozone concentration seen in test #1. In tests #2 and #3, the ozone generator was run for 120 minutes and the concentration of ozone noticeably plateaued. The air within the cell culture chamber reached a peak ozone concentration of approximately 140-150 ppm ozone. After the ozone generator was turned off, the ozone began to break down at an accelerated rate with the activated carbon filters present. In both tests #2 and #3, the ozone levels reached a level of 0.01 ppm ozone within 15 minutes.

Figure 5B:
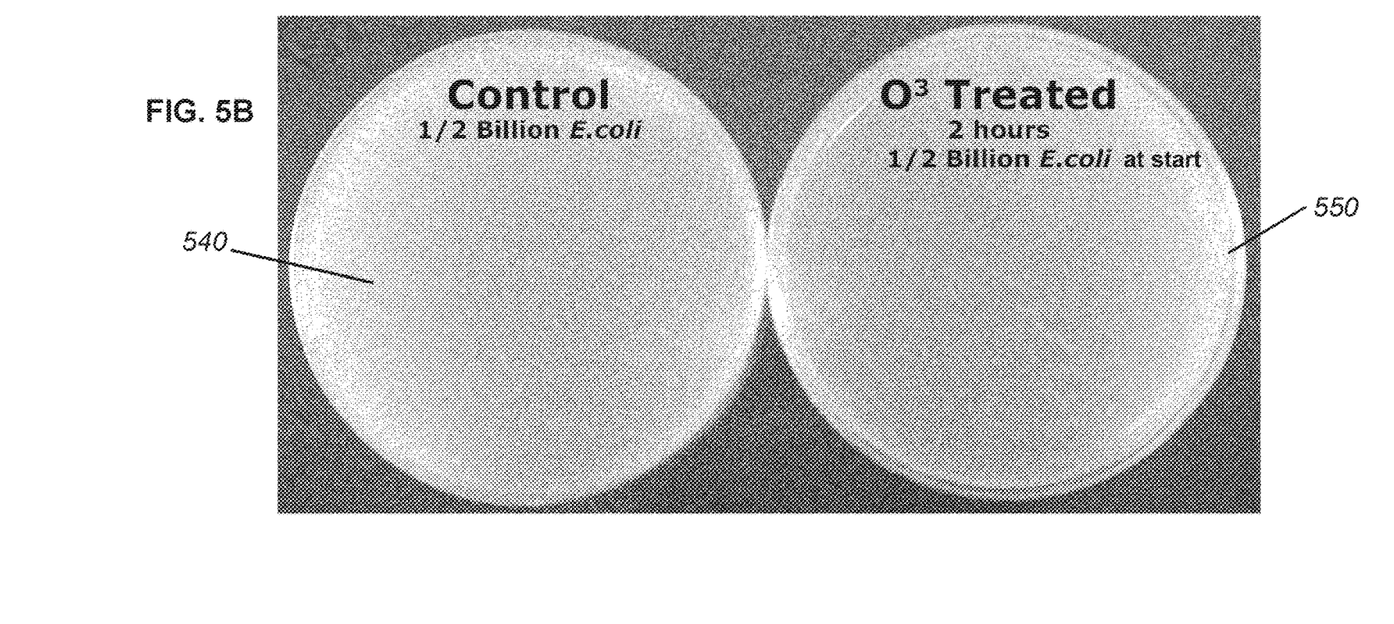
FIG. 5B provides a photograph of petri dishes demonstrating the results of an experiment testing the sterilization efficacy of one embodiment of an ozone generation and degradation unit.

While the peak ozone concentrations reached in tests #2 and #3 were noticeably lower than the peak ozone concentration of test #1, the ozone levels in tests #2 and #3 were at least sufficient to achieve sterilization. In each of tests #2 and #3, sterilization efficacy was measured with the assistance of LB agar plates loaded with $E.\ coli$ bacteria. As part of the experiment, $E.\ coli$ K-12 cells (strain DH5) were grown overnight at 37° C. and the stationary phase was reached. The following morning, 50 μL of the overnight culture (approximately $1.5\times10^8$ cells) were plated on each of three LB agar plates—two test plates and a control. A loaded agar plate was then included within each of the cell culture chambers for the duration of an ozone generation and degradation cycle (approximately 135 minutes). The agar plate was thus treated with ozone for 120 minutes and present for 15 minutes of ozone degradation within the cell culture chamber. The control plate was placed in a similar cell culture chamber for approximately 135 minutes with no ozone generator present. After each of these treatments, the plates were incubated at 37° C. overnight. The quantity of $E.\ coli$ present was then analyzed and a photograph of each plate was taken. A photograph of the control dish 540 and the test dish 550 from test #2 is provided in FIG. 5B. As seen in the photograph, in the control dish 540, the $E.\ coli$ experienced confluent growth. In the test dish 550, a 100% $E.\ coli$ kill rate was observed; no $E.\ coli$ was detected.

Experiment 2

In Experiment 2, the effect of ozone on bacteriophage T1 was studied. In the experiment, 2.5 μL of purified bacteriophage T1 was spotted in four quadrants of two LB agar plates—a test plate 610 and a control plate 620, shown in FIG. 6. The bacteriophage concentrations on each of the two plates were (clockwise from the spot in the upper right quadrant): $10^9$ pfu/mL, $10^8$ pfu/mL, $10^7$ pfu/mL, and $10^6$ pfu/mL.

Figure 6:
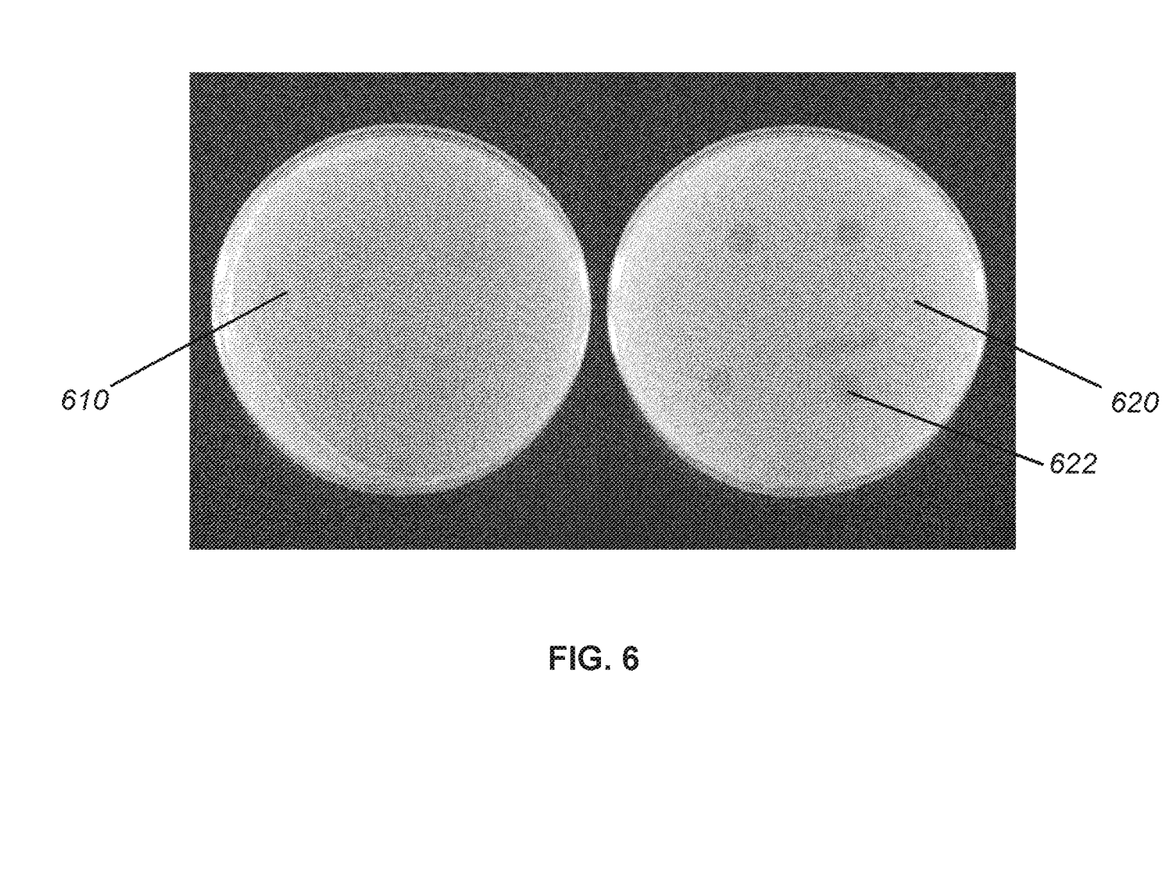
FIG. 6 provides a photograph of petri dishes demonstrating the results of an additional experiment testing the sterilization efficacy of one embodiment of an ozone generation and degradation unit.

The test plate 610 was placed in an incubator chamber containing both an ozone generator and an ozone degrader. The ozone generator included two ceramic plates surrounded substantially by a silver-coated metal mesh. The ozone generator was activated and the test plate 610 was treated with ozone for 4 hours. The ozone generator was then turned off, and the ozone degrader, formed of activated carbon filters, accelerated the conversion of ozone to oxygen. The peak ozone concentration level generated within the incubator chamber was less than 150 ppm ozone.

The control plate 620 was placed in a different incubator chamber and left untreated. After the ozone generation and degradation cycle completed in the incubator chamber containing the test plate 610, 1 mL of stationary DH5 *E. coli* bacteria and top agar were added to each plate and incubated at room temperature for 72 hours. The photograph 600 in FIG. 6 was taken immediately following this 72-hour period. As shown in FIG. 6, the control plate contained active T1-phage in all four quadrants (see the clear areas, for example, the clear spot 622). Conversely, the ozone-treated test plate 610 showed negligible survival of the T1-phage.

For purposes of summarizing the disclosure, certain aspects, advantages and features have been described herein. It is to be understood that not necessarily all such advantages may be achieved in accordance with any particular embodiment. Thus, the invention may be embodied or carried out in a manner that achieves or optimizes one advantage or group of advantages as taught herein without necessarily achieving other advantages as may be taught or suggested herein. It will also be appreciated by those of skill in the art that parts mixed with one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments. Thus, while the present disclosure has described certain practical embodiments, it is to be understood that the invention is not limited to the disclosed embodiments, but, on the contrary, is intended to cover various modifications and equivalent arrangements included within the scope of the appended claims, and equivalents thereof.

What is claimed is:

1. A method of decontaminating an enclosed space, the method comprising:
    positioning a sterilization unit of a sterilization unit system within the enclosed space, the sterilization unit comprising:
        a first housing defining an ozone generation cavity;
        a second housing defining an ozone degradation cavity;
        an ozone generator disposed within the ozone generation cavity, configured to ozonize air that enters the ozone generation cavity during an ozone generation cycle; and
        an ozone degrader disposed within the ozone degradation cavity, configured to remove ozone from air within the ozone degradation cavity during an ozone degradation cycle; and
        wherein the sterilization unit system further comprises a remote control panel configured to be separately located from the sterilization unit and outside of the enclosed space to be decontaminated, the remote control panel in wireless communication with the sterilization unit when the sterilization unit is positioned within the enclosed space, wherein commands are sent from the remote control panel to the sterilization unit when the sterilization unit is positioned within the enclosed space, wherein the remote control panel controls the length of ozone generation cycle and/or the length of the ozone degradation cycle, wherein the ozone generation cycle and the ozone degradation cycle are controlled by a user through the remote control panel positioned outside of the enclosed space when the sterilization unit is positioned within the enclosed space,
        wherein the ozone generation cycle comprises a delayed start, wherein the remote control panel provides a display of a countdown of time remaining until the ozone generation cycle is scheduled to begin when the sterilization unit is positioned within the enclosed space,
        wherein the remote control panel provides the current status of the sterilization unit during the ozone generation cycle and/or the ozone degradation cycle when the sterilization unit is positioned within the enclosed space;
    interacting with the remote control panel separately located from the sterilization unit and outside of the enclosed space to be decontaminated to send commands from the remote control panel to the sterilization unit to control a start time of the ozone generation cycle and/or a start time of the ozone degradation cycle;
    running the ozone generation cycle, comprising:
        running the ozone generation cycle to convert at least some of the oxygen into ozone within the ozone generation cavity; and
        discharging ozonized air into the enclosed space from the ozone generation cavity at least until the enclosed space reaches a first ozone concentration;
    viewing the countdown of time remaining in the ozone generation cycle on the display;
    running the ozone degradation cycle, comprising:
        running the ozone degradation cycle to convert at least some of the ozonized air into deozonized air within the ozone degradation cavity, wherein the ozone generation cycle and/or the ozone degradation cycle begin at the start time controlled by the user; and
        discharging deozonized air into the enclosed space from the ozone degradation cavity at least until the enclosed space reaches a second ozone concentration; and
    wherein the user receives information from one or more lights, visible messages, and/or audible alarms about a status of the sterilization unit during the ozone generation cycle and/or the ozone degradation cycle.

2. The method of claim 1, wherein the delayed start is a 30 minute delay.

3. The method of claim 1, wherein the remote control panel allows the user to program the delayed start when the sterilization unit is positioned within the enclosed space.

4. The method of claim 1, wherein an alarm of the remote control panel provides the user with information about a status of the sterilization unit when the sterilization unit is positioned within the enclosed space.

5. The method of claim 1, wherein the remote control panel is a cell phone.

6. The method of claim 1, wherein commands are sent from the remote control panel to the sterilization unit via Bluetooth.

7. The method of claim 1, wherein the first housing and the second housing are not enclosed within a same outer housing and are located a distance away from each other at different locations within the enclosed space.

8. The method of claim 1, wherein the first housing defining the ozone generation cavity is located near a top of the enclosed space to be decontaminated, and the second housing defining the ozone degradation cavity is located near a base of the enclosed space.

9. The method of claim 1, wherein a processor of the sterilization unit system is programmed to calculate a run time for the ozone generation cycle.

10. The method of claim 1, wherein the sterilization unit comprises one or more sensors configured to detect humidity, pressure, or temperature.

11. The method of claim 1, wherein the sterilization unit comprises one or more sensors configured to detect a current ozone level in the enclosed space.

12. The method of claim 1, wherein the method does not require generation of steam.

13. The method of claim 1, wherein the method does not require generation of heat.

14. The method of claim 1, wherein the method does not require that the enclosed space fully seals in gases.

15. The method of claim 1, wherein the first ozone concentration is above 0.1 ppm.

16. The method of claim 1, wherein the second ozone concentration is below 0.1 ppm.

17. The method of claim 1, wherein the enclosed space is an automobile.

18. The method of claim 1, wherein different enclosed spaces undergo different ozone generation cycles.

* * * * *